United States Patent [19]

Donadelli

[11] 4,312,340
[45] Jan. 26, 1982

[54] METHOD FOR RESTORING OPTIMUM SKIN CONDITIONS, ESPECIALLY FOR PARTIALLY OR ENTIRELY HEALING INTRADERMAL TEARS

[76] Inventor: Franco Donadelli, Via Bronzino, 6, Milan, Italy

[21] Appl. No.: 893,075

[22] Filed: Jun. 7, 1978

Related U.S. Application Data

[63] Continuation-in-part of Ser. No. 869,032, Jan. 6, 1978, abandoned.

[30] Foreign Application Priority Data

Apr. 7, 1977 [IT] Italy .................... 22185 A/77

[51] Int. Cl.³ ............................................. A61N 1/30
[52] U.S. Cl. ................................. 128/207.21; 128/421
[58] Field of Search ......... 128/207.21, 419 R, 421–423, 128/803

[56] References Cited

U.S. PATENT DOCUMENTS

| | | | |
|---|---|---|---|
| 2,263,205 | 11/1941 | Conrad | 128/207.21 |
| 3,964,477 | 6/1976 | Ellis et al. | 128/207.21 |
| 4,141,359 | 2/1979 | Jacobsen et al. | 128/207.21 |

FOREIGN PATENT DOCUMENTS

| | | | |
|---|---|---|---|
| 1278065 | 10/1961 | France | 128/207.21 |
| 596246 | 3/1978 | U.S.S.R. | 128/207.21 |

*Primary Examiner*—Lee S. Cohen
*Attorney, Agent, or Firm*—Michael J. Striker

[57] ABSTRACT

In a method of treatment of cicatrized human skin, a variable electric field of low frequency is applied to the skin thereby creating an electric charge below the injured area. Simultaneously a solution is applied onto the surface of the scarred skin and also generating an electric field. The two electric fields are adapted to react together in such a manner that a proteinic synthesis is obtained, wherein the solution is subjected to a chemical and electrical pretreatment in order to provide the suitable electric field.

9 Claims, 12 Drawing Figures

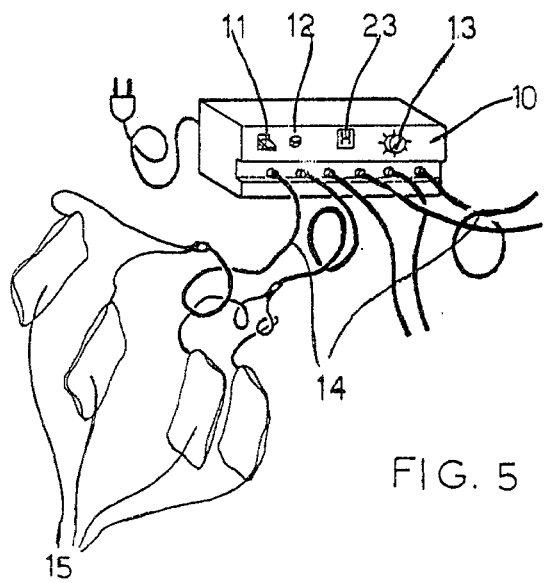
FIG. 5
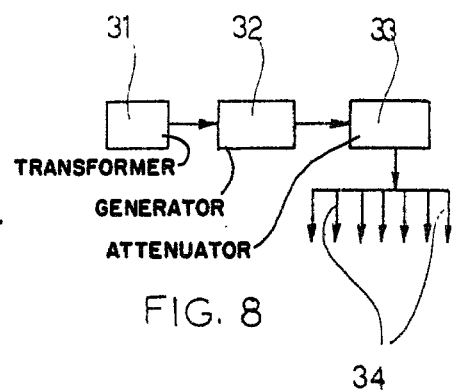
FIG. 8
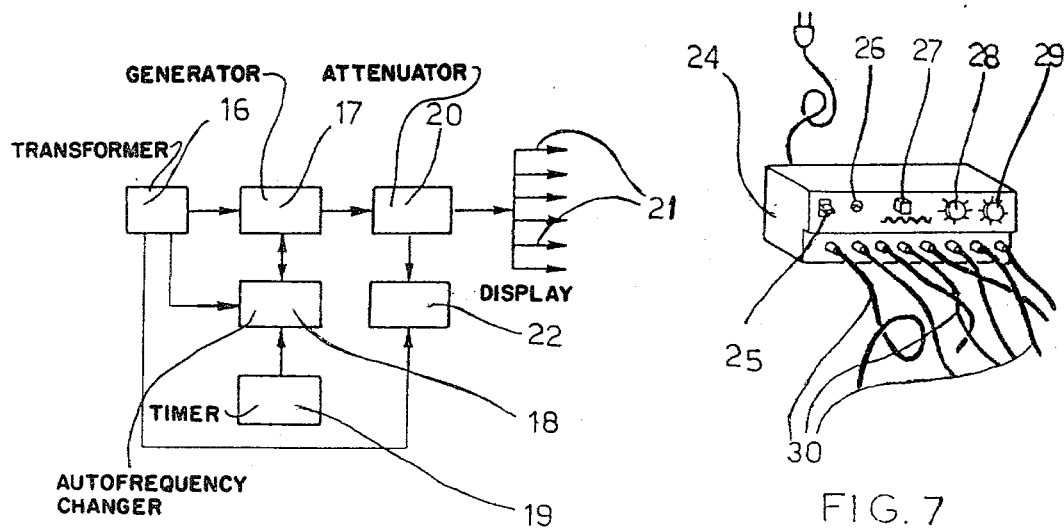
FIG. 6
FIG. 7

METHOD FOR RESTORING OPTIMUM SKIN CONDITIONS, ESPECIALLY FOR PARTIALLY OR ENTIRELY HEALING INTRADERMAL TEARS

CROSS-REFERENCE TO RELATED APPLICATION

This application is a continuation-in-part of application Ser. No. 869,032 filed Jan. 6, 1978 and entitled "Process for restoring optimum skin conditions, especially for partially or entirely healing intradermal tears (Striae gravidarum) by simultaneous application of a variable electric field and a solution of skin-regenerating extracts and ionized catalysts", now abandoned.

BACKGROUND OF THE INVENTION

Field of the Invention

This invention relates to a method for restoring optimum skin conditions especially for healing intradermal tears and more particularly to a method of applying electrical and chemical treatment to a scarred area of the skin.

In normal skin the collagen fibrilles are constant in size and lie parallel one to another, while in healed scars the fibres are of different sizes and lie in all directions. From the histological point of view intradermal tears represent the external part of a dermic wound and, subsequently, of a dermic cicatrix.

A number of methods are known utilized to assist regeneration of open skin tissue (lesions) or of partially broken tissues as in the case of intradermal tears and similar kinds. Such methods include, for example, application of vegetable extracts, scorching with electromagnetic waves at high frequency plastic surgery, exposure to an electromagnetic field combined with a simultaneous treatment with irradiated water.

Especially in the case of intradermal tears, all these methods, some of which are difficult and painful to apply, have shown themselves to be only partially effective or entirely ineffective. Such methods as exposure to weak electric fields or application of saline or ammine solutions, protein and embryionic tissues have been found absolutely ineffective.

SUMMARY OF THE INVENTION

It is an object of this invention to stimulate the cicatrized skin to restore the tissue continuity.

Another object of this invention is to assist the fibres to dispose parallel and compactly.

These objects are achieved by applying a proteinic solution made from tissue regenerating extracts to the skin and applying a low frequency sinusoidal electric field to the scarred area of the skin so as to give an electric charge to the layers underlying the lesions. The proteinic solution applied to the cicatriced skin is subjected to an electrical and chemical pretreatment including a partial electrolysis process to provide a formation of groups of aminoacids in the solution and to successively apply a low-frequency alternating electric field on said solution to form clusters of ionized molecules.

BRIEF DESCRIPTION OF THE DRAWINGS

FIG. 5 is a perspective view showing an apparatus for generating an electric field in the derm;

FIG. 6 is a diagrammatic view of an electrical scheme of the apparatus shown in FIG. 5;

FIG. 7 is a perspective view of an apparatus for producing a proteinic solution which is applied to a scarred skin in accordance with the present invention; and FIG. 8 is a diagrammatic view of an electrical scheme of the apparatus shown in FIG. 8.

DETAILED DESCRIPTION OF THE PREFERRED EMBODIMENT

Figure 1A:
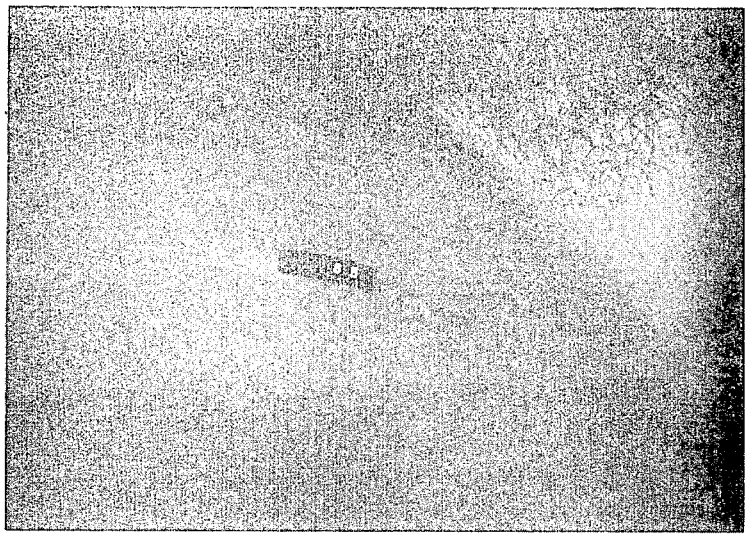
FIG. 1A is a photographic view showing intradermal tears on the left thigh of a 30 year old woman.

It is well known that the stage of passing over to cell reproduction requires a failure of internal cohesion and activation of proteinic synthesis, namely an increase in the concentration of the S-H groups (primary factors of proteinic synthesis). It is considered that all these changes are caused by an alteration in balance between electron "donors" and "receivers" which facilitates a breakdown between S-S and disulphide links and the formation of active S-H links.

It is a known fact that the S-S links have a degree of energy equivalent to about 63 Kcal/mol, while that of the S-H links reach the energy equivalent about 87 Kcal/mol.

It has been found by experiment that, in an electric or magnetic field, a solution of polypeptides forms clusters of rectilinear molecules, orientated in the direction of the field in respect of their bipolar moment. Each cluster is composed of polymerized molecules parallel to the direction of the electric field.

The needed energy by applying a double electric field is one to the surface level of the skin and the second one to the dermic level is supplied to the cicatrized skin which is stimulated causing a breakdown of the S-S links and formation of the S-H links.

The first electric field is obtained in accordance to the present invention by application of a proteinic solution made from tissue regenerating extracts to the surface layer of the skin. The solution which includes a substance existing in the skin itself is prepared from a composition of embryonic placenta, collagen and vitreous humor extracts diluted in distilled water. This solution is subjected to a treatment preceeding its applying to a cicatrized skin.

The pretreatment of the solution includes an electrolysis process which lasts for several days (about 5). An electrolysis reaction is set up in the solution by two gold electrodes connected to a square wave electric field generator. A low frequency alternating electric field is then applied to the solution for another period of about 5 days (frequency below 10,000 Hz). The substance of the solution by partial electrolysis are split up into groups of aminoacids. By applying an electric field clusters of molecules are formed in the solution and a successive electrical excitation (ionization) of the most active groups with an increased electrical moment of the molecules themselves.

The second electric field is obtained in accordance with the present invention by applying a low frequency alternating electric field to the scarred area of the skin in such a way as to give an electric charge to the layers underlying the lesions. The effect of this double electric field is that the molecules forming the solution and those in the electrically charged layers of the skin, react together producing something very like an electromagnetic "mirror" effect and involving the skin in this reaction throughout its whole depth.

FIGS. 5 and 6 illustrate an apparatus for generating an electric field in the derma layer of the scarred skin. The apparatus includes a container 10, a front panel of which carries a switch 11 connected to the apparatus to the mains, a pilot light 12, a knob 13 to change a field voltage from 1 to 9 volt, 6 outputs 14 carrying current to 6 pairs of electrodes 15 covered with sponges. FIG. 6 depicting an electrical scheme of the apparatus shown in FIG. 5 includes a transformer 16 connected to the mains supplies current at a maximum of 9 V to the sinusoidal wave generator 17 the frequency of which is automatically changed in cycles by an automatic frequency changer 18 served by a timer 19. Through a signal attenuator 20 the sinusoidal waves pass to the outputs 21. A display 22 (shown in FIG. 5 by a reference 23) shows actual voltage values.

The frequency in accordance with 60" sweeps between 1.5 and 4 KHz, or in accordance with other values as the case may be, is automatically changed through the above described circuits.

An apparatus for producing the solution is applied to the surface layer of the skin as shown in FIGS. 7 and 8. The apparatus is held in container 24 a front panel of which carries a switch 25 to connect the apparatus to mains and a pilot light 26. A key 27 enables a passage to be made from a square wave field to a sinusoidal wave field. A knob 28 serves to change the frequency on the apparatus and a knob 29 is adapted to change the voltage on the apparatus. Outputs 30 are connected to the pairs of electrodes for treating the solution. The diagram of the electric circuits shown in FIG. 8 illustrates a transformer 31 connected to the mains and to a sinusoidal and square wave generator 32 to supply the latter with current at 15 to 20 volt. From the generator a signal passes to a signal attenuator 33 and from there to the pairs of outputs 34. A treatment of a patient is provided by applying the electrodes 15 departing from the electric field generator. The electrodes 15 are covered with sponge material and damped with "aqua fortis" to which 1 ml of solution is added and applied in counterposed pairs to the boundaries of the area of the skin. Utilizing half of the maximum voltage (4 or 5 V), the skin is charged for 20 to 30 minutes with a weak electric field the intensity of current applied to the skin being less than 10 microwatt/cm$^2$. The electrodes are then removed and the part is damped with a few ml of solutions. This treatment is repeated two or three times a week. The first results may be seen after a month or two. During the treatment of a patient the following steps may be added in preparation of the above-described solution:

addition to the solution of small quantities (1–2×1,000) of glycine and methianine to assist the formation of the S-H groups;

dilution of the solution with $\frac{1}{3}$ N101-vol of double distilled glycerine after the electrical and chemical treatments, in order to get an even film on the skin;

addition to the solution—after the initial phase of partial electrolysis—of catalysts corresponding to the following two groups: vitamins (traces of E, C, H, PP) and metals (zinc, magnesium, cobalt and other ions).

FIGS. 1A through 4B show the advantages obtained as a result of utilization of the treatment in accordance with the present invention.

Figure 1B:
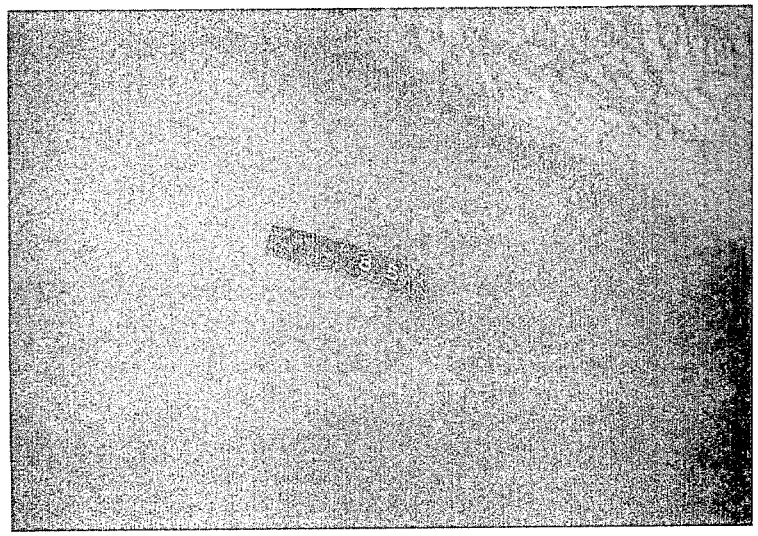
FIG. 1B is a photographic view illustrating the thigh in FIG. 1A after three months of treatment in accordance with the present invention.
Figure 2A:
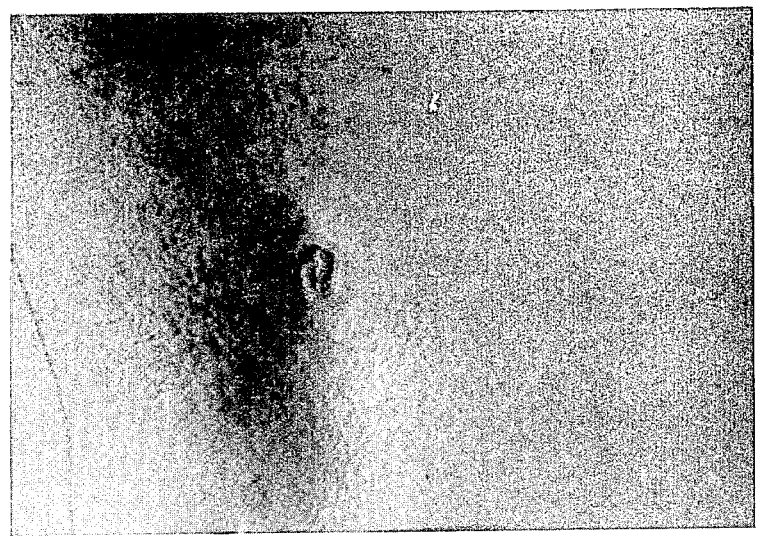
FIG. 2A is a photographic view of an abdomen of a 27-year old women showing anarea healed by many intradermal tears.
Figure 2B:
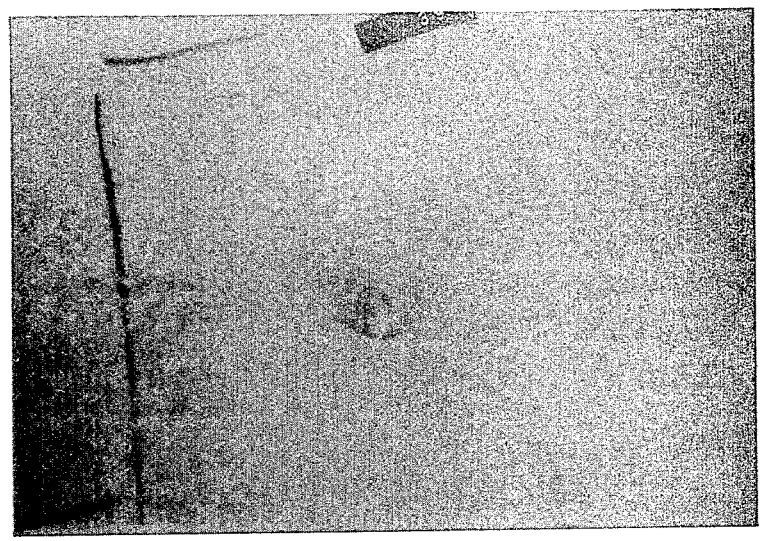
FIG. 2B is a photographic view of the abdomen illustrated in FIG. 2A after four months of treatment.
Figure 3A:
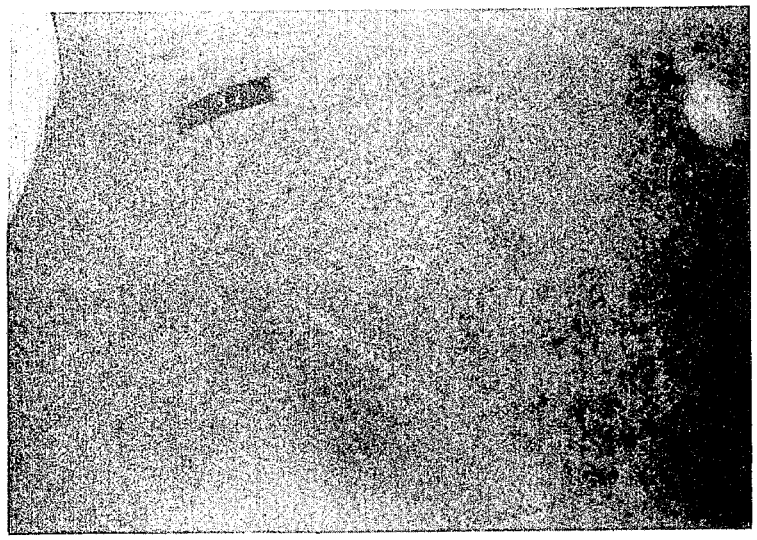
FIG. 3A is a photographic view of an abdomen of a 30-year old women prior to the treatment.
Figure 3B:
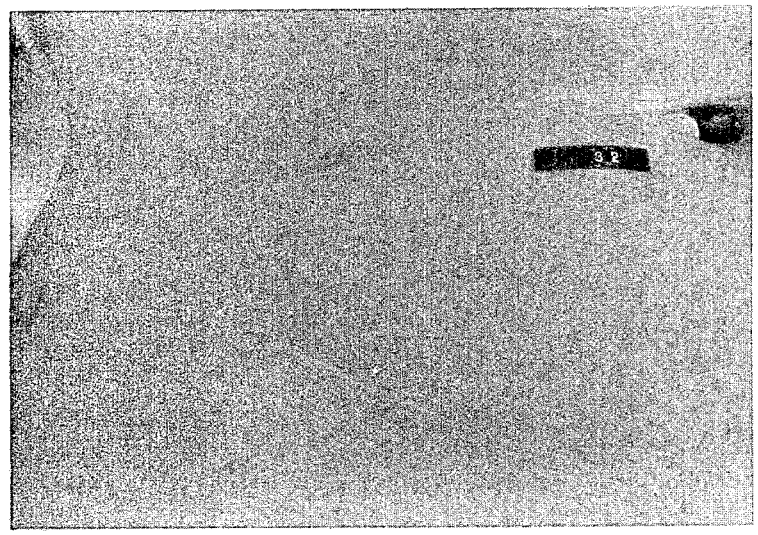
FIG. 3B illustrates the abdomen shown in FIG. 3A after three months of treatment.
Figure 4:
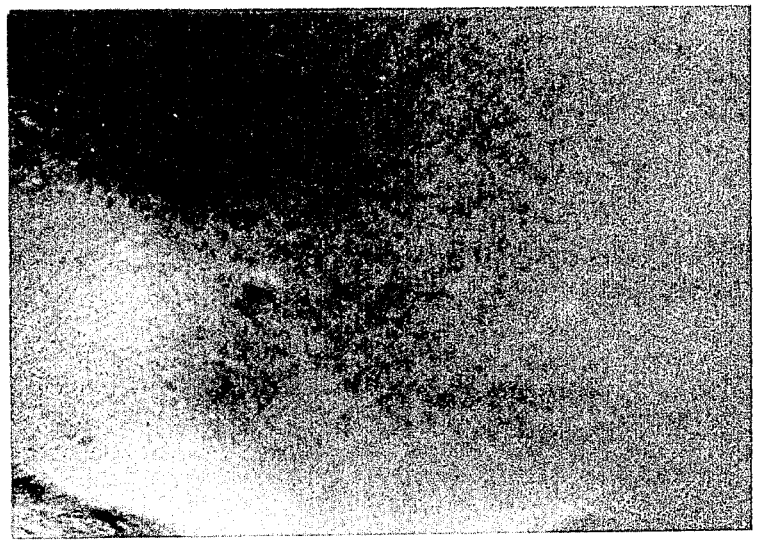
FIG. 4A is a photographic view showing the post chicken-pox scars on a face of a 25-year old person.
FIG. 4B is a photographic view of the scars shown in FIG. 4A after 7 months of treatment.
Figure 4:
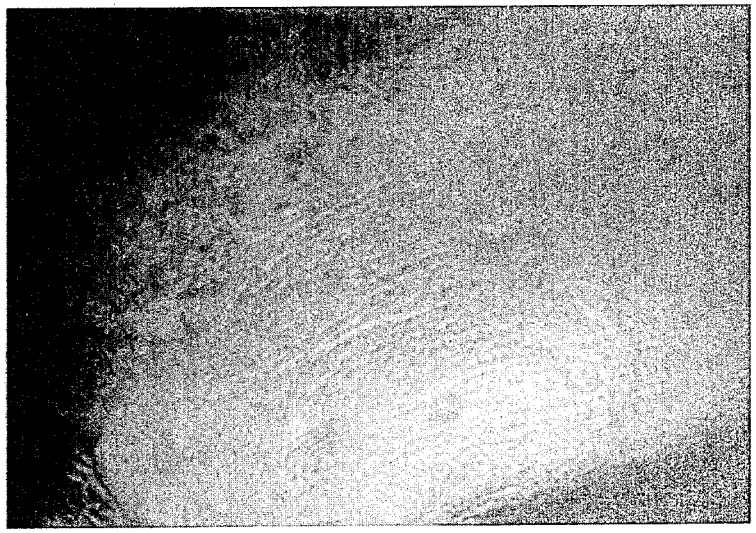

FIGS. 1A, 1B; 2A, 2B and 3A, 3B and 4A and 4B illustrate the parts of a human body before and after the treatment. In the pock marks, still visible after treatment, the presence of parallel fibres, undoubtedly like those in ordinary skin tissue, can be seen. The above photographs, as well as all the experience in practical application hitherto gained, confirm the validity of the invention and all the advantages it can offer.

The results obtained in a considerable number of experiences and applications have fully born out the theoretical approach hereinabove described achieving elimination, or reduction of the cicatrices and lesions and forming real regenerated tissue.

As the ways of using the invention have been described merely as examples of application, but in no way limited to these, it remains understood that every equivalent application of the concepts described and every equivalent product put into effect and/or in operation are protected by the terms of the patent application.

I claim:

1. A method of treatment of cicatrized human skin, comprising applying at a derma level of a scarred area underlying the cicatrized skin a low-frequency non-ionizing variable electric field for a predetermined time and simultaneously applying an aqueous proteinic solution made of tissue-regenerating extracts to a surface level of said scarred area so that the scarred area is located between the electric field and the solution thereby provoking a reaction leading to proteinic synthesis, said solution being prior to its application to the human skin subjected to a chemical and electrical pre-treatment which includes exposing the solution to an electrolysis reaction for a number of days and subsequently applying a low-frequency alternating electric field to the solution for a number of days, to thereby eliminate or reduce discontinuities in the skin caused by cicatrices, lesions and intradermal tears.

2. The method of treatment of claim 1, wherein said aqueous solution is selected from the group consisting of extracts of embryonic, placenta, collagen and humor vitreous.

3. The method of claim 1, wherein in subjecting of said solution to the electrolysis reaction, after subjecting said solution to said reaction for a predetermined time to obtain a partial electrolysis reaction, a catalyst is added to the solution, the catalyst being selected from the group consisting of vitamins E, C, H, PP, zinc, magnesium and cobalt as well as a combination thereof.

4. The method of treatment of claim 1, wherein the electric field is applied to the scarred area of the skin by means of at least one pair of electrodes placed onto the edges of the scarred area of the skin.

5. The method of treatment of claim 4, wherein said electrodes are covered with sponge material.

6. The method of treatment of claim 5, wherein said solution is applied onto the skin by preliminary soaking said sponge material in said solution.

7. The method of treatment of claim 4, wherein said solution is directly applied onto the skin.

8. The method as set forth in claim 1, wherein said applying a low frequency non-ionizing variable electric field at a derma level of the scarred area and said applying an aqueous proteinic solution to a surface level of said scarred area are carried out with two or three weekly applications continuing for a few months and wherein said low-frequency variable electric field is applied at each sitting for 20-30 minutes.

9. The method as set forth in claim 1, wherein said electric field applied to a derma level is obtained by application of alternating current at a maximum voltage of 9 V, and with 60-second sweeps between 1.5 and 4 KHz by using pairs of electrodes placed at the boundaries of the area of the skin to be treated, the intensity of current applied being less than 10 micro-watt/cm$^2$.

* * * * *